(12) United States Patent
Afilani

(10) Patent No.: US 6,411,099 B1
(45) Date of Patent: Jun. 25, 2002

(54) SELECTIVE POLARIZATION MATCHING FILTER WITH AN ELECTRET FOR TRIGGERING AND OPTIMIZING RAPID DIELECTROKINESIS RESPONSE

(75) Inventor: Thomas L. Afilani, Jersey Shore, PA (US)

(73) Assignee: DKL International, Inc., Wilmington, DE (US)

( * ) Notice: Subject to any disclaimer, the term of this patent is extended or adjusted under 35 U.S.C. 154(b) by 0 days.

(21) Appl. No.: 09/537,391

(22) Filed: Mar. 29, 2000

Related U.S. Application Data

(63) Continuation-in-part of application No. 08/840,069, filed on Apr. 24, 1997, now Pat. No. 6,078,179.

(51) Int. Cl.⁷ .......................... G01N 27/00; G08B 23/00
(52) U.S. Cl. ........................................ 324/457; 324/452
(58) Field of Search ................................. 324/452, 457, 324/458, 71.1, 72; 340/572

(56) References Cited

U.S. PATENT DOCUMENTS

| | | | | |
|---|---|---|---|---|
| 3,771,152 A | * | 11/1973 | Dettling et al. ............. | 340/562 |
| 4,198,620 A | * | 4/1980 | Vogt et al. .................. | 367/199 |
| 5,019,804 A | * | 5/1991 | Fraden ........................ | 340/562 |
| 5,288,306 A | * | 2/1994 | Aibe et al. .................... | 95/141 |
| 5,405,434 A | * | 4/1995 | Inculet ........................... | 96/54 |
| 5,436,054 A | * | 7/1995 | Tani et al. ................... | 428/131 |
| 5,748,088 A | * | 5/1998 | Afilani ....................... | 340/573 |
| 5,907,280 A | * | 5/1999 | Afilani ..................... | 340/573.1 |

OTHER PUBLICATIONS

Dale W. Murray, "Physical Examination of the DKL Life-Guard Model 3" Sandia National Laboratories, pp 1–25, Oct. 1998.*

* cited by examiner

Primary Examiner—N. Le
Assistant Examiner—T. R. Sundaram
(74) Attorney, Agent, or Firm—Nixon & Vanderhye P.C.

(57) ABSTRACT

A composition of matter utilizes a pre-polarized ("poled" or previously subjected to a strong DC voltage with or without an external elevated temperature) step converting the matter into an electret state with long-lasting polarization (weeks/months/years) or into a ferroelectric state with permanent polarization. The dielectric replicate matching reference material is used to make a detection device component that triggers and maximizes, when the poled, pre-polarized material/component is subject to externally initiated spinning (set in rotary motion by the detection device's human operator), a dielectrokinesis (phoresis)-like phenomena (force, torque) in exactly the opposite manifestation of the operative mode of dielectrokinesis (phoresis) compared to that which occurs when the component and material are not pre-polarized (poled), both of which can be used to detect the presence of specific entities of a predetermined type that contain as a major component the matching dielectric material. The exactly opposite manifestation of the operative mode phenomena exhibited by the poled material/component is self-extinguishing in that, when placed in a specific detection device, and the poled component is not spun, the poled component exhibits dielectrokinesis-like phenomena (force, torque) in exactly the same manifestation of the operative mode as that exhibited by non-poled, non-pre-polarized components. Different designs and materials of construction for the detection device component enable the detection of a variety of specific entities including human beings, animals, plastics, metals, water, etc. Detectors using specific combinations of poled and non-poled components and materials can detect and localize the line-of-bearing position presented by a specific entity irrespective of the presence or absence of any type intervening visual obstructuring material structures or barriers, lighting conditions, weather conditions or electromagnetic interference (EMI).

31 Claims, 5 Drawing Sheets

SELECTIVE POLARIZATION MATCHING FILTER WITH AN ELECTRET FOR TRIGGERING AND OPTIMIZING RAPID DIELECTROKINESIS RESPONSE

This application is a continuation-in-part of copending U.S. patent application Ser. No. 08/840,069, Apr. 24, 1997, now U.S. Pat. No. 6,078,179, issued Jun. 20, 2000, the entire content of which is hereby incorporated by reference.

BACKGROUND OF THE INVENTION

This invention relates to the fields of dielectrokinesis (phoresis), dielectric relaxation dynamics, electronic devices and systems and, more particularly, to a selective polarization matching filter for triggering and maximizing the dielectrokinesis response in the detection of specific entities consisting of organic and inorganic materials via detection of a force or replenishment energy density of stored electrical energy.

The detection of the presence or absence of specific entities—human beings, plastics (mixtures of various polymers and with additives) and other organic/inorganic materials—irrespective of the presence of intervening vision-obstructing structures or EMI signals has uses in very diverse applications such as: (a) fire fighting and rescue; (b) national border security; (c) transportation security in pre-boarding planes, trains and automobiles; (d) new and old construction industry; (e) law enforcement; (f) military operations; (g) anti-shoplifting protection; (h) other security and emergency needs and operations, etc.

It is known that humans, animals and other animate species generate an external electric field and gradients thereof. For example, in human physiology, the central and peripheral nervous system neurons, the sensory system cells, the skeletal muscular system, as well as the cardiac conduction cells and cardiac muscle system cells all operate by a depolarization and repolarization phenomena occurring across their respective cellular membranes, which are naturally in a dielectric polarization state.

The trans-membrane ion currents and potentials utilizing $Na^{+1}$, $K^{+1}$ ions, etc., all work to establish a resting potential across the cell membranes that can be characterized as a high state of polarization. The ion concentration (moles/cm$^3$) within and surrounding the unmyelinated cell axon establish the resting potential. The fluids themselves are neutral. What keeps the ions on the membrane is their attraction for each other across the membrane. Independent of this process the $Cl^{-1}$ ions tend to diffuse into the cell since their concentration outside is higher. Both the $K^{+1}$ and $Cl^{-1}$ diffusion tend to charge the interior of the cell negatively and the exterior of the cell positively. As charge accumulates on the membrane surface, it becomes increasingly difficult for more ions to diffuse. $K^{+1}$ ions trying to move outward are repelled by the positive charge already present. Equilibrium is reached when the tendency to diffuse because of the concentration is balanced by the electrical potential difference across the membrane. The greater the concentration difference, the greater the potential difference across the membrane. The resting potential can be calculated by the Nernst Equation, wherein the potential $(V)=V_{Inside}-V_{Outside}$ such that:

$$\text{Voltage(potential)} = 2.30 \frac{kT}{ze} \log \frac{Co}{Ci}$$

where Co and Ci are ion concentrations inside and outside, k is the Boltzmann constant, T is absolute temperature, e is the charge on the electron and z is the valence (number of electron charges) on the ion.

The nerve and conduction impulses, as well as the sensory, cardiac, and muscular action potentials and subsequent responses are manifested via sequential periodic pulses (waves) resulting in first rapid depolarization and, shortly after, rapid repolarization to reestablish the rest state, namely, the original polarization state of the membrane. The transverse membrane ion currents produce a dipole charge that moves along the cell membrane. The greater the stimulus the more the pulses that are produced along the membrane.

The action potentials are related to the ratio of the respective ion concentrations inside and outside the different types of membranes. The resultant polarization electrical field distribution pattern has a high degree of spatial non-uniformity and can be characterized as a bound dipolar charge distribution pattern. A detailed discussion of the human generated electric field can be found in R. A. Rhodes, *Human Physiology*, Harcourt Brace Javanovich (1992) and D. C. Gianocoli, *Physics Principles with Applications*, Prentice Hall (1980), the teachings of which are hereby incorporated by reference.

Alternatively, the external electric field and gradients thereof can be supplied by an external source via static electrification for use with inanimate targets such as plastics, metals, water, etc.

It would be advantageous to be able to detect the external electric field and gradients thereof, either generated naturally by an animate species or induced by an external source, on an entity specific basis. It would further be advantageous to enable this detection at great distances and through obstructions. It has been discovered that such detection is possible using the selective polarization matching filter in accordance with the present invention in conjunction with the principles of dielectrophoresis.

Dielectrophoresis describes the force upon and mechanical behavior of initially neutral matter that is dielectric polarization charged via induction by external spatially non-uniformity electric fields. The severity of the spatial non-uniformity of the electric field is measured by the spatial gradient (spatial rate of change) of the electric field. A fundamental operating principle of the dielectrophoresis effect is that the force (or torque) in air generated at a point and space in time always points (or seeks to point) in the same direction, mainly toward the maximum gradient (non-uniformity) of the local electric field, independent of sign (+ or −) and time variations (DC or AC) of electrical fields (voltages) and of the surrounding medium dielectric properties.

The dielectrophoresis force magnitude depends distinctively nonlinearly upon the dielectric polarizibility of the surrounding medium, the dielectric polarizibility of initially neutral matter and nonlinearly upon the neutral matter's geometry. This dependence is via the Clausius-Mossotti function, well-known from polarizibility studies in solid state physics. The dielectrophoresis force depends nonlinearly upon the local applied electric field produced by the target. The dielectrophoresis force depends upon the spatial gradient of the square (second power) of the target's local electric field distribution at a point in space and time where a detector is located. The spatial gradient of the square of the local electric field is measured by the dielectrophoresis force produced by the induced polarization charge on the detector. This constant-direction-seeking force is highly variable in magnitude both as a function of angular position (at fixed radial distance from the target) and as a function of the radial position (at a fixed angular position) and as a function of the "effective" medium polarizibility. The force's detection signature is a unique pattern of the target's spatial gradient of the local electric field squared, with the detector always pointing (seeking to point) out the direction of the local maximum of the gradient pattern. All experimental results and equations of dielectrophoresis are consistent with the fundamental electromagnetic laws (Maxwell's equations).

It is conventional for initially neutral matter to exhibit regular "para-electric" (closely related to) phenomena called dielectrophoresis (i.e., force and torque pivots the initially neutral matter to align itself with the spatial position of the local maximum spatial gradient of the external electric field squared), however, this need not always be the case. The normal para-electric dielectrophoresis response is generally the result of a two-step process: (1) induced polarization of the initially neutral matter by the external electric field pattern, followed by (2) action of the spatially non-uniform external electric field pattern upon the induced dipole within the neutral matter to produce a conventional para-electric dielectrophoresis force and torque rotating the neutral matter around a pivot line in order to align the long dimension of the neutral matter with the spatial position of the maximum spatial gradient of the external electric field squared.

An exact opposite operative mode of the dielectrophoresis phenomena occurs, an unconventional "apo-electric" (away from; separate) electric dielectrophoresis force and torque can arise if, for example, the initially neutral matter has already been both (1) previously strongly pre-polarized (e.g., permanent dipole ferroelectric material (such as $BaTiO_3$, $PbTiO_3$ or $Ba_xSr_yTiO_3$ (where x+y=1), etc.) or a long lasting dipole electret material (such as Carnauba wax, Teflon™ (polytetrafluoroethylene), or Mylar™ (polyethyleneterephthalate), etc.) both made by "poling" or subjecting the neutral matter to a strong external DC voltage with or without an external, elevated temperature) and (2) the neutral matter is being spun about an axis of rotation. The apo-electric dielectrophoresis force and torque rotates the "poled" neutral matter around a pivot line in order to align the long dimension of the neutral matter with the spatial position of the local minimum spatial gradient of the external electric field squared. The apo-electric response is self-extinguishing in that, when the "poled" neutral matter is made to stop spinning, the poled neutral matter now exhibits para-electric dielectrophoresis phenomena (force, torque) in exactly the same operative mode as exhibited by non-poled, non-prepolarized neutral matter (rotation to point toward the local maximum spatial gradient of the external electric field squared).

The unconventional apo-electric dielectrophoresis response is the strongest when the axis of rotation of the ferroelectric or electret material is at a right angle to the external electric field direction. The apo-electric dielectrophoresis response is negligible if the axis of rotation is parallel to the external field direction. The apo-electric response will thus occur only for the component of the external electric field perpendicular to the axis of rotation. The application of an external electric field to a material system capable of making an unconventional, apo-electric dielectrophoresis response increases the energy state of the system. The application of para-electric dielectrophoresis response decreases the energy state of the system. The source of energy in both situations is the entity (human operator) providing the spinning of the poled materials and sampling of the external electric field spatial gradient pattern.

The apo-electric unconventional dielectrophoresis response, although predicted many years ago has not yet been observed for macroscopic bodies (like humans), H. A. Pohl, *J. Electrochemical Society*, 115, 155c (1968). On the molecular size scale, for example, an apo-electric dielectrophoresis-type response is used in a vital step in the maser/laser operation to artificially shift the population of excited states before the masing/lasing effect begins (C. H. Townes, Science, 149, 831 (1965)).

There are five known modes of dielectric polarization. These include: electronic polarization, where electron distribution about the atom nuclei is slightly distorted due to the imposed external electric field; atomic polarization, where the atom's distribution within initially neutral matter is slightly distorted due to the imposed external electric field; nomadic polarization, where in very specific polymers, etc., highly delocalized electron or proton distribution is highly distorted over several molecular repeat units due to the imposed external electric field; rotational polarization (dipolar and orientational), where permanent dipoles ($H_2O$, NO, HF) and orientable pendant polar groups (—OH, —Cl, —CN, —$NO_2$) hung flexibly on molecules in material are rotationally aligned toward the external electric field with characteristic time constants; and interfacial (space charge) polarization, where inhomogeneous dielectric interfaces accumulate charge carriers due to differing small electrical conductivities. With the interfacial polarization, the resulting space charge accumulated to neutralize the interface charges distorts the external electric field with characteristic time constants.

The first three modes of dielectric polarization, electronic, atomic and nomadic, are molecular in distance scale and occur "instantaneously" as soon as the external electric field is imposed and contribute to the dielectric constant of the material at very high frequencies (infrared and optical). The last two polarization modes, rotational and interfacial, are molecular and macroscopic in distance scale and appear dynamically over time with characteristic time constants to change (usually increase) the high frequency dielectric response constant toward the dielectric constant at zero frequency. These characteristic material time constants control the dielectric and mechanical response of a material.

The modes of polarization and their dynamics in contributing to the time evolution of dielectric constants are discussed in various publications, such as H. A. Pohl, *Dielectrophoresis*, Cambridge University Press (1978); R. Schiller *Electrons in Dielectric Media*, C. Ferradini, J. Gerin (eds.), CRC Press (1991), and R. Schiller, *Macroscopic Friction and Dielectric Relaxation*, IEEE Transactions on Electrical Insulation, 24, 199 (1989). See also, Herbert A. Pohl, *Dielectrophoresis: The Behavior of Neutral Matter in Non-Uniform Electric Fields*, Cambridge University Press (1978). A. D. Moore (Editor), *Electrostatics and its Applications*, Chapters 14 and 15 (Dielectrophoresis), Wiley/Interscience (1973), pages 336–376. These teachings are hereby incorporated by reference.

SUMMARY OF THE INVENTION

The present invention relates to a modified selective polarization matching filter formed of compositions of matter using a pre-polarization ("poled" or previously subjected to a strong external DC voltage with or without an external, elevated temperature) step, converting the initially neutral material into an electret state with long-lasting polarization (weeks/months/years) or into a ferroelectric state with permanent polarization. The composition of matter serves as a dielectric replicate matching reference material that is used to make a detection device component that triggers and maximizes, when the poled, pre-polarized material/ component is also subject to externally initiated spinning (set in rotary motion), an apo-electric dielectrokinesis (phoresis) phenomena (force, torque) occurring in an exact opposite operative mode of the dielectrophoresis phenomena to that which occurs when the component and material are not pre-polarized (poled), and a conventional para-electric dielectrokinesis (phoresis) phenomena occurs, where both operative modes can be used to detect the presence of specific entities of a predetermined type that contain as a major component the matching dielectric material (poled or non-poled). The modified, selective polarization filter is an important element in triggering and also maximizing both the mechanical torque and energy replenishment modes using dielectrokinesis (phoresis) methods to detect entities.

The exact opposite operative mode of the dielectrokinesis phenomena exhibited by the poled material or component is self-extinguishing in that, when placed in a specific detection device, and the poled component is not spinning, the poled component exhibits dielectrokinesis (force, torque) in exactly the same operative mode as that exhibited by non-poled, non-pre-polarized components. Different designs and materials of construction for the detection device component enable the detection of a variety of specific entities including human beings, animals, plastics, metals, water, etc. Detectors are effective using specific combinations of poled and non-poled components and materials irrespective of the presence or absence of any type of intervening visual obstructing material structures or barriers, lighting or weather conditions or electromagnetic interference (EM).

A non-poled selective polarization matching filter of the copending application noted above is formed of compositions of matter using initially neutral material chosen to be an exact dielectric replicate of an entity to be detected via dielectrokinesis (phoresis). The filter is an important element in triggering and also maximizing both the mechanical torque and energy replenishment modes using dielectrokinesis (phoresis) methods to detect entities.

This filtering action of either construction applies to a practically limitless range of materials to be detected as an entity of interest target. The detection materials include, for example, nano-structured human keratin protein polymer for human detection, nano-structured animal keratin protein polymer for animal detection, specific plastic (mixture of polymers and additives) for plastic detection, and the like. The dielectric replicate material comprising the selective polarization filter functionally performs a spatial dielectric property matching between the entity of interest and a locator device to locate the entities. The filter enables the device to operate using the dielectrokinesis (phoresis) phenomena to specifically detect only those entities matching the dielectric response signature of the polarization filter component. The dielectric signature includes both the dielectric constant and dielectric loss frequency spectra and all characteristic time constants controlling the polarization evolution/mechanics in external electric fields.

There are two primary elements for the dielectrokinesis entity location detection device to operate. The first element is an external electric field and spatial gradients thereof, and the second element is the selective dielectric polarization matching filter of the present invention. As noted above, the external electric field and gradients thereof can be provided by the entity of interest itself as is the case when animate species are the entities of interest to be detected. Alternatively, the external electric field and gradients thereof can be supplied by an external source via static electrification as is the case when inanimate entities are the entities of interest to be detected.

The selective polarization matching filter embodied in this invention can be used in the detection device itself as either a passive or active circuit component (no flowing or flowing continuous electric current, respectively). The selective polarization matching filter embodied in this invention can be used with conventional electronic components (resistors, capacitors, inductors, transistors, etc.) in the overall operational design of the type of locator device used to detect the presence or absence of a specific entity of a predetermined type.

BRIEF DESCRWIION OF THE DRAWINGS

Other advantages and objects of the present invention will be described in detail with reference to the accompanying drawings, in which.

DETAILED DESCRIPTION OF PREFERRED EMBODIMENTS

The external electric field and gradients thereof of the target entity defines a specific polarization pattern for the entity. In order to detect the target entity electric field and gradients thereof, it is necessary to impart an opposite polarization pattern on a detector element such as an antenna or the like. The selective polarization matching filter according to the present invention serves as a matching bridge between the detector operator and the opposite polarized detector component to generate the opposite polarization pattern.

Figure 1:
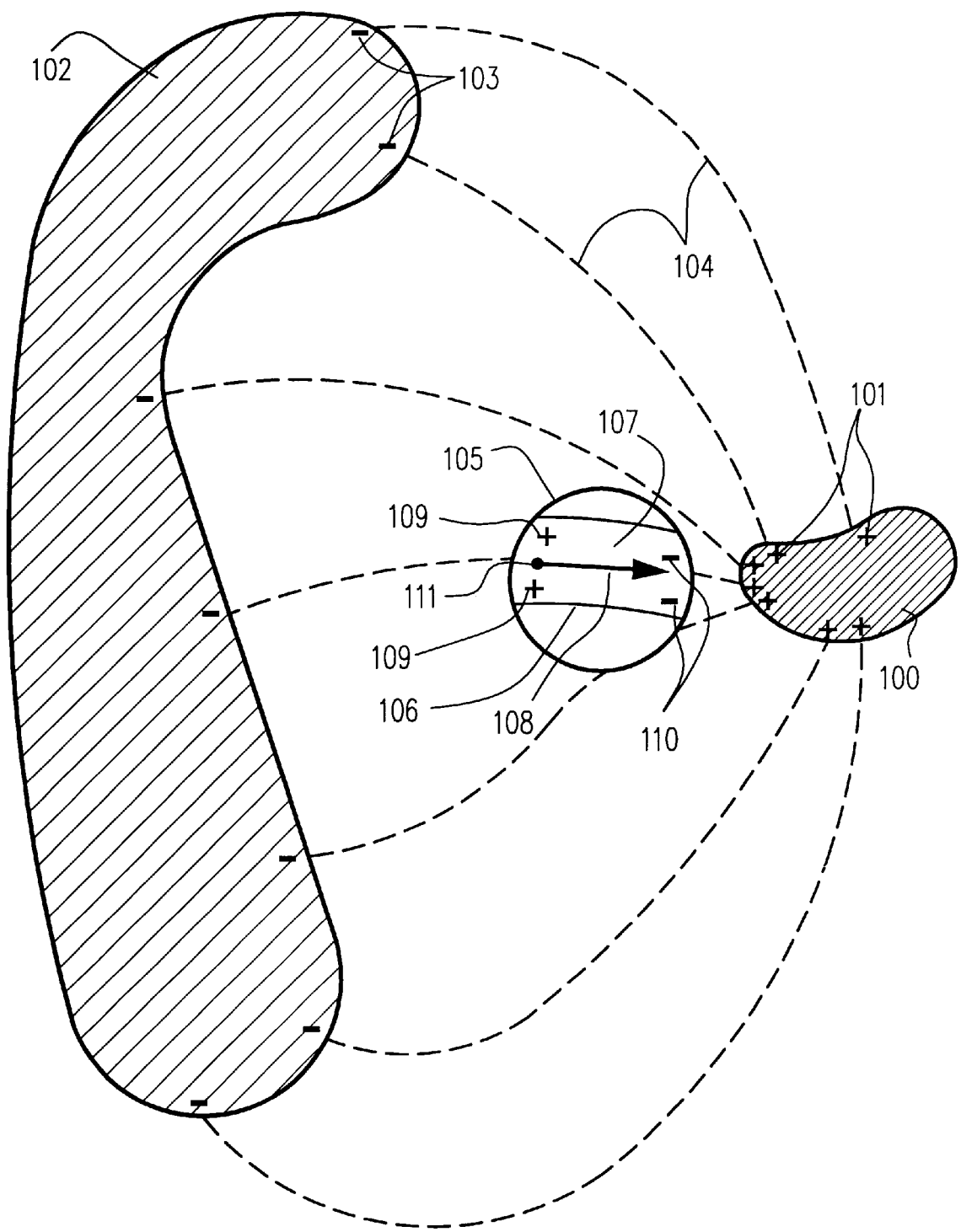
FIG. 1 is a schematic drawing of an entity, a ground plane, the locating device using the non pre-polarized neutral matter for a para-electric selective polarization filter according the copending invention and the entity's polarization electric field lines.

FIG. 1 shows a target entity of interest 100 and a surrounding ground plane 102. The entity's polarization charges 101 produce non-uniform electric field lines 104 that have a unique spatial pattern as shown. The non-uniform electric field lines also have a unique spatial gradient pattern (not shown). The non-uniform electric field lines 104 terminate on the surrounding ground plane 102 and induce opposite polarization charges 103 thereon. An initially neutral matter or medium 105, such as the device of the copending application, is shown amidst the non-uniform electric field lines. The neutral matter 105 includes a cavity 106 filled with a specific dielectric material 107. The non-uniform electric field lines induce polarization charges 109 and 110 in the dielectric material 107. The neutral matter 105 also contain protuberant antennas to form a pivot line 111 that is perpendicular to the plane containing FIG. 1. The para-electric dielectrophoretic-like force manifests itself as an easily detected torque motion of the antennas 108 about the pivot line 111 as the initially neutral matter or medium 105, of the copending application is moved (is rotated or is spun by the detection device's human operator) as the device samples the non-uniform electric field lines 104. The protuberant antennas 108 generate torque to align themselves with the maximum spatial gradient of the electric field lines 104.

Figure 2:
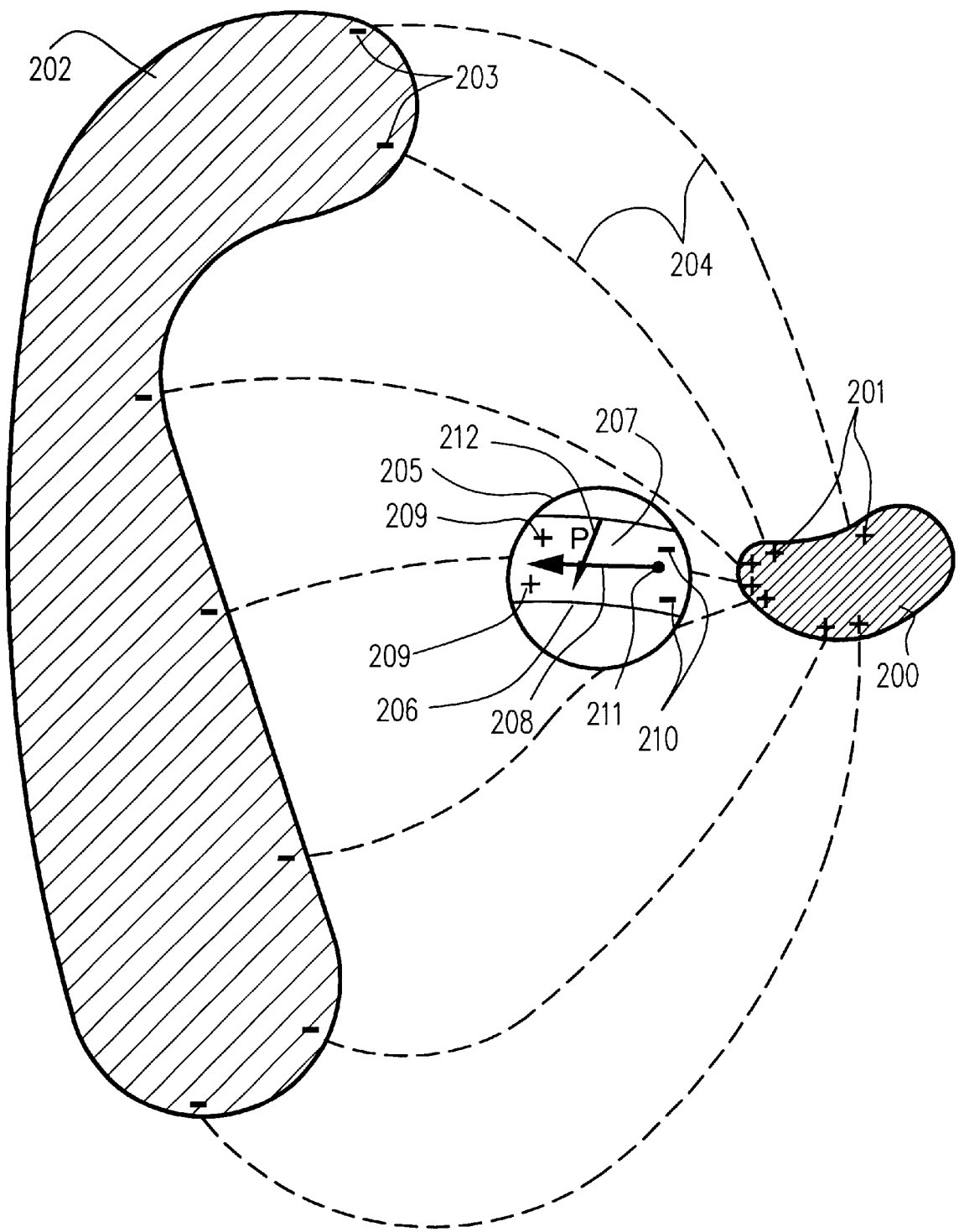
FIG. 2 is a schematic drawing of an entity, a ground plane, the locating device using the pre-polarized neutral matter for an apo-electric selective polarization filter according to the present invention and the entity's polarization electric field lines.

FIG. 2 shows a target entity of interest 200 and a surrounding ground plane 202. The entity's polarization charges 201 produce non-uniform electric field lines 204 that have a unique spatial pattern as shown. The non-uniform electric field lines 204 also have a unique electric field spatial gradient pattern (not shown). The electric field lines terminate on the surrounding ground plane 202 and induce opposite polarization charges 203 thereon. An initially neutral matter or medium 205, such as the device of the present invention, is shown amidst the non-uniform electric field lines. The neutral matter 205 includes a cavity 206 filled with a specific dielectric material 207. The non-uniform electric field lines induce polarization charges 209 and 210 in the dielectric material 207. The neutral matter 205 also contains protuberant antennas that form a pivot line 211 perpendicular to the plane containing FIG. 2. The apo-electric dielectrophoretic-like force manifests itself as an easily detected torque motion of the antennas 208 about the pivot line 211 as the poled or pre-polarized material or medium 205, of the present invention, is moved (is rotated or is spun by the detection device's human operator) as the device samples the non-uniform electric field lines 204. The manifestation of the force and torque is in an exact opposite operative mode and phenomena compared to the conventional para-electric case due to the presence of the pre-polarization P 212 for the apo-electric case. The protuberant antennas 208 generate torque to align themselves with the spatial positions of the minimum spatial gradient of the electric field lines 204 as long as the apo-electric selective polarization filter of the present invention and the device containing it are still being rotated or spun or scanned by the detection device's human operator to sample the electric field lines 204. Once rotation stops, the antennas generate torque to realign themselves with the local maximum spatial gradient of the electric field pattern. The apo-electric case is therefore self-extinguishing and flip-flops from alignment to the local minimum to alignment to the local maximum spatial gradient of the electric field squared pattern.

Figure 3:
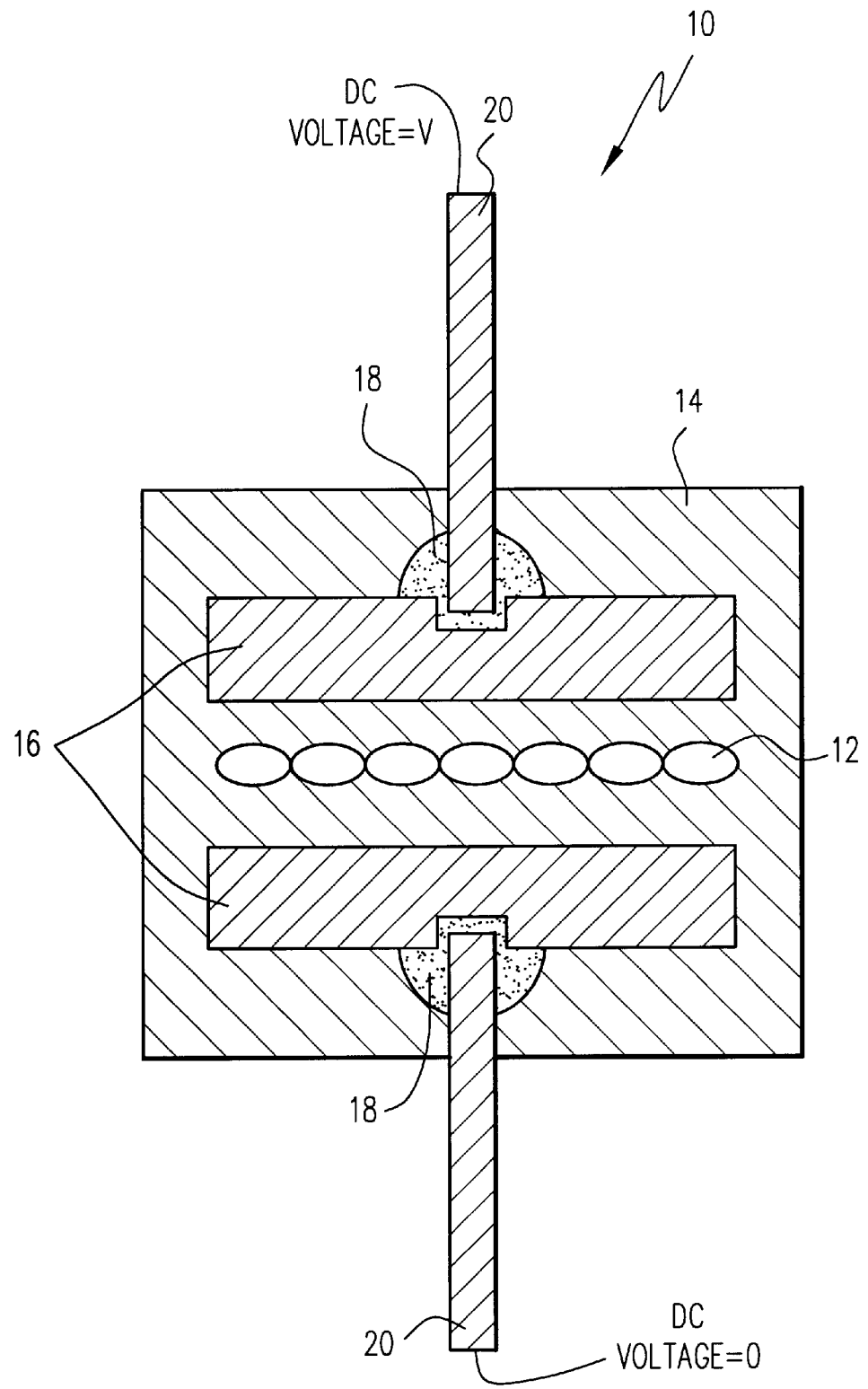
FIG. 3 is a schematic illustration of a first embodiment apo-electric pre-polarized selective polarization matching filter produced by subjecting the filter to a high DC voltage acc to the present invention.
Figure 4:
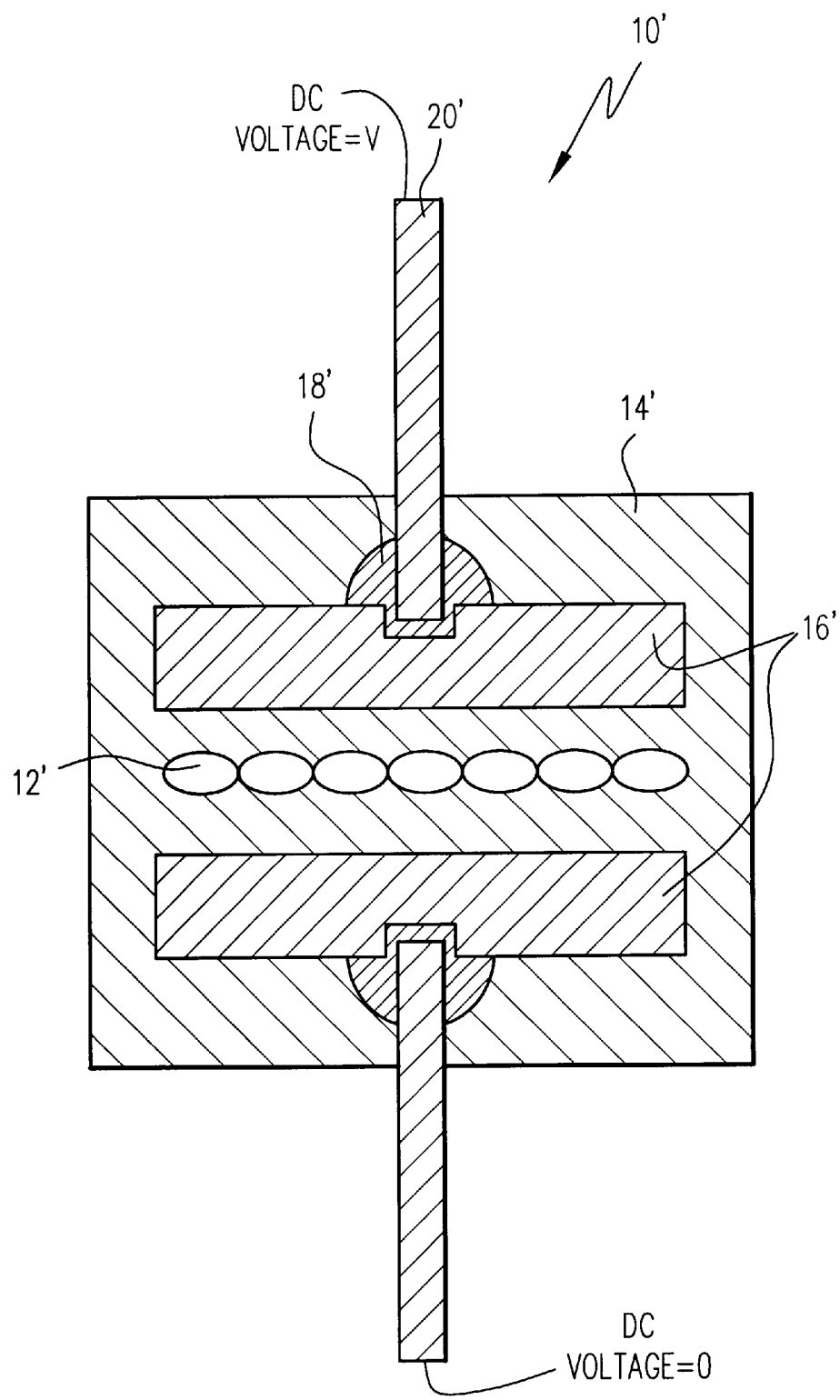
FIG. 4 is a schematic illustration of a second embodiment apo-electric pre-polarized selective polarization matching filter according to the present invention.
Figure 5:
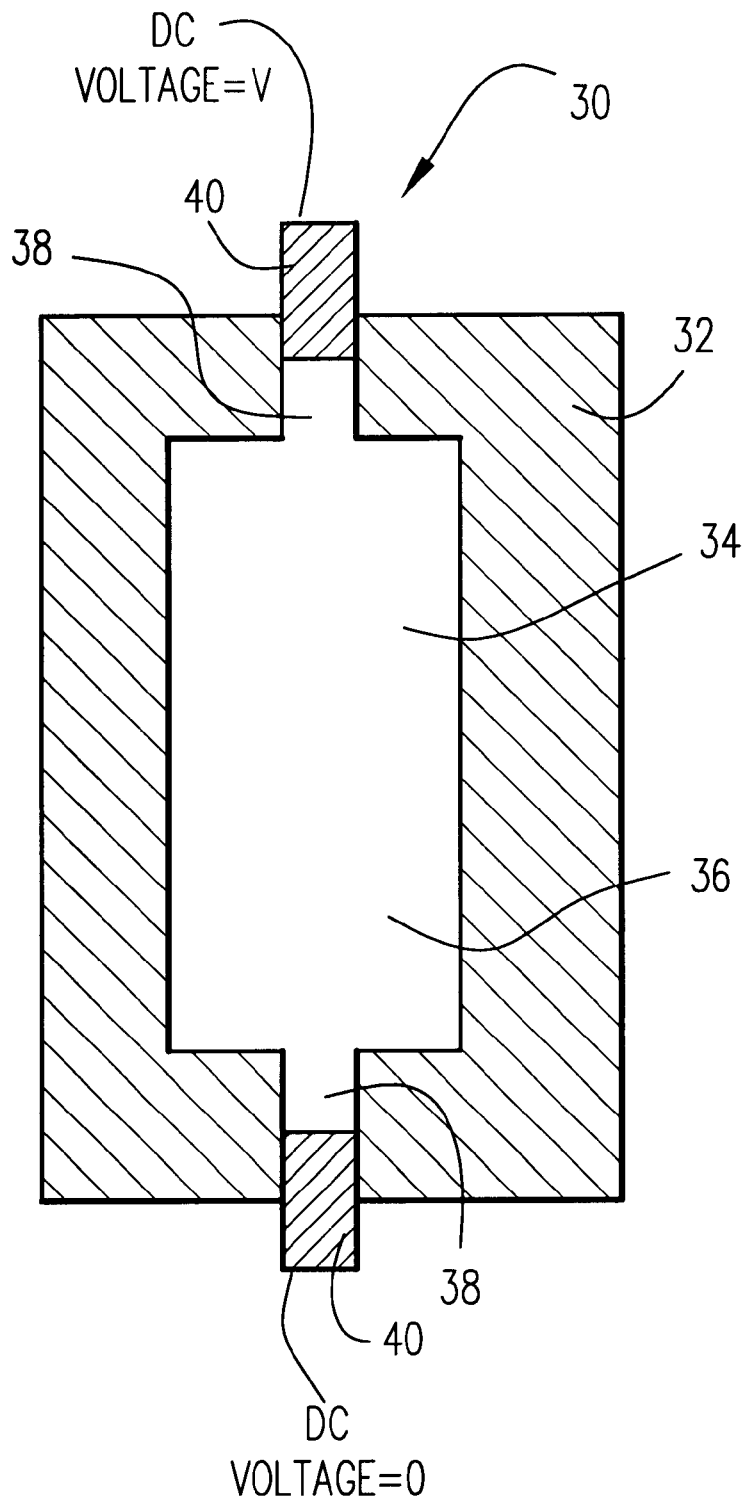
FIG. 5 is a schematic illustration of a third embodiment apo-electric pre-polarized selective polarization matching filter according to the present invention.

In FIGS. 3, 4 and 5, the poling step takes place by attaching one "hot" electrical lead (DC voltage=V) from the high voltage generating equipment to one of the metallic electrical leads of each of the three specific selective polarization filter designs and the second "cold or ground" leads (DC voltage=0) of the high voltage equipment to the second metallic electrical lead to each of the three specific selective polarization filter designs.

It has been discovered that specific combinations of materials provide the desired effects of the selective polarization filter. FIG. 3 illustrates the filter according to a first embodiment of the invention for non-electrically conducting materials. As shown in FIG. 3, the filter 10 includes a replicate dielectric property matching material 12 encapsulated within a filter body 14 formed of a polymer such as polyurethane. A pair of parallel plates 16 disposed enclosing the replicate dielectric property matching material 12 are also encapsulated in the filter housing 14. The plates 16 are preferably formed of a different polymer such as acrylonitrile-butadiene-styrene (ABS). In this arrangement, the plates 16 are coupled with metal electrical leads 20 via isocyanate glue pods 18 or the like.

The replicate dielectric property matching material 12 is selected in accordance with the characteristics of the entity to be detected. That is, the replicate property matching material contains identical dielectric properties, time constants and related macroscopic friction coefficients to those of the entity material to be detected. Examples of suitable replicate dielectric property matching materials include nano-structured human keratin protein polymer for human detection, nano-structured animal keratin protein polymer for animal detection, specific plastic (mixture of polymers and additives) for plastic detection and the like.

With reference to FIG. 4, in a second embodiment for electrically conducting replicate materials, the structure is substantially similar to that of the first embodiment. The plates 16' in the filter 10', however, are formed of metal such as copper, brass, aluminum or steel. The metal plates 16' are connected to the electrical leads 20' via solder pods 18'. Examples of suitable conducting replicate property matching materials include, for example, gold, silver, platinum, palladium and iron.

In a third embodiment, referring to FIG. 5, for non-electrically conducting replicate materials, the replicate dielectric property matching material itself is utilized as the filter housing. As shown in FIG. 5, the filter 30 according to the third embodiment of the invention includes a filter housing 32 formed of the replicate dielectric property matching material and defining therein a cavity 34. Another dielectric material 36 such as air is disposed in the cavity 34. Exit ports 38 from the cavity 34 are formed in the filter housing 32 and are filled with a conducting material 40, preferably of metal, coupled with an external electronic circuit connector and grounding terminals (not shown).

The dielectrokinesis (phoresis) phenomena can be used with the current dielectric polarization matching filter disclosure of the invention in at least two methodologies to enable the detection and location of specific entities of interest. The first methodology utilizes the dielectrophoresis force directly. This is usually observed via a torque "action at a distance" motion acting around a well-defined pivot point and line. An example of this application is described in commonly owned, co-pending patent application Ser. No. 08/758,248, the disclosure of which is hereby incorporated by reference.

The second methodology is where a dielectric replicate of the material of interest to be detected is provided with an external electric field and spatial gradients thereof by external static electrification. This allows a measurable electrical energy replenishment to occur when a second material, dielectrically matching the replicate reference material, comes within close proximity to the reference material and undergoes polarization by the external electric field provided by the static electrification.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

What is claimed is:
1. A selective polarization matching filter comprising:
   a filter housing formed of a first material;
   a replicate property matching material disposed encapsulated within said filter housing, said replicate property matching material being in an electret or ferroelectric state after having been subjected to pre-polarization; and a pair of substantially parallel plates disposed encapsulated within said filter housing on opposite sides of said replicate property matching material, said plates being formed of a second material different from said first material.

2. A selective polarization matching filter according to claim 1, further comprising a pair of grounding leads disposed coupled to said plates, respectively, and extending to an exterior of said filter housing.

3. A selective polarization matching filter according to claim 1, wherein said first material is a polymer, said second material is a polymer different from said first material, and said replicate property matching material is a dielectric material.

4. A selective polarization matching filter according to claim 3, wherein said first material is polyurethane.

5. A selective polarization matching filter according to claim 4, wherein said second material is acrylonitrile-butadiene-styrene.

6. A selective polarization matching filter according to claim 5, wherein said replicate property matching material is selected in accordance with dielectric polarization characteristics of a to-be-detected entity.

7. A selective polarization matching filter according to claim 6, wherein said replicate property matching material comprises one of nano-structured human keratin protein polymer, nano-structured animal keratin protein polymer, or a polymer blend.

8. A selective polarization matching filter according to claim 3, wherein said second material is acrylonitrile-butadiene-styrene.

9. A selective polarization matching filter according to claim 3, wherein said replicate property matching material is selected in accordance with dielectric polarization characteristics of a to-be-detected entity.

10. A selective polarization matching filter according to claim 9, wherein said replicate property matching material comprises one of nano-structured human keratin protein polymer, nano-structured animal keratin protein polymer, or a polymer blend.

11. A selective polarization matching filter according to claim 1, wherein said first material is a polymer, said second material is metal, and said replicate property matching material is a conducting material.

12. A selective polarization matching filter according to claim 11, wherein said first material is polyurethane.

13. A selective polarization matching filter according to claim 12, wherein said second material is one of copper, brass, aluminum and steel.

14. A selective polarization matching filter according to claim 13, wherein said replicate property matching material is selected in accordance with dielectric polarization characteristics of a to-be-detected entity.

15. A selective polarization matching filter according to claim 14, wherein said replicate property matching material is one of gold, silver, platinum, palladium or iron.

16. A selective polarization matching filter according to claim 1, wherein said replicate property matching material is selected in accordance with dielectric polarization characteristics of a to-be-detected entity.

17. A selective polarization matching filter according to claim 16, wherein said replicate property matching material is one of nano-structured human keratin protein polymer or nano-structured animal keratin protein polymer.

18. A selective polarization matching filter according to claim 16, further comprising an auxiliary attachment containing one of 2-propanol or 2-methyl-2-propanol operatively cooperating with the filter.

19. A selective polarization matching filter comprising:
a filter housing formed of a replicate dielectric property matching material, said filter housing defining a cavity therein having a pair of exit ports, wherein said replicate property matching material is in an electret or ferroelectric state after having been subjected to pre-polarization;

a dielectric material disposed in said cavity, said dielectric material being different from said replicate dielectric matching material; and a pair of conducting inserts disposed in said exit ports, respectively, said conducting inserts extending to an exterior of said filter housing.

20. A selective polarization matching filter according to claim 19, wherein said dielectric material disposed in said cavity is air.

21. A selective polarization matching filter according to claim 19, further comprising an auxiliary attachment containing one of 2-propanol or 2-methyl-2-propanol operatively cooperating with the filter.

22. A selective polarization matching filter comprising a composition of materials configured to generate an opposite polarization pattern based on a polarization pattern of a to-be-detected entity, wherein at least one material of the composition of materials is in an electret or ferroelectric state after having been subjected to pre-polarization.

23. A selective polarization matching filter according to claim 22, wherein said composition of materials comprises a replicate property matching material selected in accordance with dielectric polarization characteristics of the entity to be detected, and wherein the at least one of the composition of materials comprises the replicate property matching material.

24. A selective polarization matching filter according to claim 23, wherein said composition of materials further comprises at least one dielectric material.

25. A selective polarization matching filter according to claim 22, wherein said composition of materials comprises acrylonitrile-butadiene-styrene (ABS) disposed encapsulated in polyurethane.

26. A selective polarization matching filter according to claim 25, wherein said composition of materials further comprises a replicate dielectric property matching material disposed encapsulated in said polyurethane and enclosed by said ABS.

27. A method of manufacturing a selective polarization matching filter comprising:
assembling a composition of materials to generate an opposite polarization pattern based on a polarization pattern of a to-be-detected entity; and pre-polarizing at least one of the composition of materials into an electret or ferroelectric state.

28. A method according to claim 27, wherein said assembling step comprises encapsulating a replicate property matching material selected in accordance with dielectric polarization characteristics of the entity to be detected in a dielectric material, and wherein the at least one of the composition of materials comprises the replicate property matching material.

29. A method according to claim 28, wherein the assembling step further comprises encapsulating a pair of substantially parallel plates in the dielectric material and enclosing the replicate property matching material with the plates.

30. A method according to claim 27, wherein the pre-polarizing step comprises applying an external voltage.

31. A method according to claim 30, wherein the step of applying an external voltage is practiced with an elevated temperature.

* * * * *